United States Patent [19]
Kloepper et al.

[11] Patent Number: 5,640,803
[45] Date of Patent: Jun. 24, 1997

[54] ENHANCEMENT OF CONIFER SEEDLING GROWTH

[75] Inventors: Joseph W. Kloepper, Auburn, Ala.; Elizabeth M. Tipping, Georgetown, Canada

[73] Assignee: Agrium, Inc., Calgary, Canada

[21] Appl. No.: 269,359

[22] Filed: Jun. 30, 1994

Related U.S. Application Data

[63] Continuation of Ser. No. 768,566, Apr. 28, 1992, abandoned, and a continuation of Ser. No. 347,731, May 5, 1989, abandoned.

[51] Int. Cl.$^6$ .............................. A01C 1/06; A01C 21/00; A01N 63/00
[52] U.S. Cl. .................. 47/57.6; 424/93.4; 424/93.47; 71/6
[58] Field of Search .................... 424/93 D, 93.4, 424/93.47; 47/57.605, 57.6; 71/6; 800/200

[56] References Cited

FOREIGN PATENT DOCUMENTS

WO88/09114 12/1988 WIPO.
WO90/13219 11/1990 WIPO.

OTHER PUBLICATIONS

Pokojska–Burdziej (1982) Polish Journal of Soil Science 15:137–143.

Ralston et al. (1976) Plant and Soil 45:493–507.

Kloepper et al. (Jan. 1988) Plant Disease 72:42–46.

Chanway et al. (1991) Soil Biol. Biochem. 23:575–580.

Lifshitz et al. (1986) Appln. Env. Microbiol. 51:251–255.

*Primary Examiner*—David T. Fox
*Assistant Examiner*—Elizabeth C. Kemmerer
*Attorney, Agent, or Firm*—Fitzpatrick, Cella, Harper & Scinto

[57] ABSTRACT

A method for growing a conifer seedling includes selecting and treating a conifer seed, prior to planting thereof, with a Coryneform, Pseudomonas or Serratia bacterial strain that enhances the root growth of that conifer seedling. Additionally, transplanted conifer seedlings may be grown by treating their roots with root growth-enhancing Coryneform, Pseudomonas and Serratia strains and conifer seeds may be modified by treatment with those strains.

16 Claims, No Drawings

ENHANCEMENT OF CONIFER SEEDLING GROWTH

This application is a continuation of application Ser. No. 768,566, filed Apr. 28, 1992, now abandoned, and is also a continuation of application Ser. No. 347,731, filed May 5, 1989, now abandoned.

BACKGROUND OF THE INVENTION

Various strains of saprophytic soil microorganisms am known to influence plant growth in different types of plants. Increases in yield of agronomic crop plants (angiosperms), for example, can be obtained through inoculation with strains of selected soil bacteria. Among the bacteria that exhibit beneficial effects on crop plant development, perhaps the most promising are those which characteristically colonize the surface of the plant roots. As distinct from other plant-beneficial soil isolates that inhabit the area surrounding the root, the "root-colonizers" i.e. rhizobacteria, are able to transfer from seed inoculated therewith to mots developing from the seed, and are able to maintain a stable and growth-promoting association with the growing root system of the crop plant.

Since theft discovery, members of the plant growth promoting rhizobacteria (PGPR) family have been shown to exhibit a wide range of beneficial effects on agronomic crops. One group of these root-colonizers is capable of exerting growth promoting effects directly on the plant; another group, the biocontrol PGPR, is capable of reducing the influence of pathogens in the root zone (see Kloepper et al, 1988, ISI Atlas of Science: Animal and Plant Sciences, pp. 60–64; and see Davison, 1988, Bio/Technology, 6, pp. 282–286). The plant growth promoting rhizobacteria have also been shown to exhibit beneficial effects on seedlings of fruit trees, such as apple trees (Ceasar and Burr, 1987, Phytopathology, 77, pp. 1583–1588) and citrus trees including rough lemon and sweet orange.

The possibility of employing beneficial microorganisms as inocula is also being researched by the forestry industry and, in particular, by the conifer industry which is responsible for supplying the vast numbers of conifer seedlings required annually for outplanting to reforestation sites. Conifer nurseries currently experience a seedling mortality rate of approximately 30% in the greenhouse, owing to poor germination, disease and other factors causing stunted seedling growth. Of those conifer seedlings grown successfully in the greenhouse, a further 18–50% either cannot survive or fail to establish after planting at the reforestation site.

Of particular interest to the conifer seedling industry are microbial agents capable of enhancing the rate at which the nursery-grown seedlings mature, and microbial agents that act, more specifically, to enhance development of the coffer seedling root and shoot system both in the greenhouse and during the critical growth stages which follow outplanting of those seedlings in the field. However, since microorganisms capable of promoting these beneficial effects on seedling growth must be capable also of tolerating the harsh i.e. cold and acidic, soils in which the seedlings are ultimately planted, the search for candidate microorganisms has been particularly demanding.

To identify microorganisms capable of surviving at the conifer root zone, Kampert et al (Polish Journal of Soil Science, 1975, 8(3): 59–66) inoculated conifer seed and seedlings with forest soil and then studied the microbial flora resident in the seedling root zone. Their studies revealed that only a limited variety of microbial species contained in the soil inocula were capable of inhabiting the seedling rhizosphere. More particularly, they found that while the rhizosphere was colonized by various species of fungi such as Fusarium, Penicillium and Trichoderma, the colonizing bacteria were limited almost exclusively to those of the Coryneform group. Though the Coryneforms were capable of colonizing the conifer seedling root zone, subsequent studies revealed that inocula containing the Coryneforms caused a reduction, rather than an increase, in the length of pine seedling roots and shoots.

Ectomyccorhizzae species capable of inhabiting the conifer root zone, such as the Fusarium sp., are currently showing some promise as inocula beneficial to conifer seedling growth. While the mechanism through which the ectomycorrhizae offer these advantages is not well understood, it is believed that the ectomycorrhizal mantle (a sheath of ectomycorrhizal hyphae) that forms around the conifer roots serves to protect the root from pathogens and/or provides for enlargement of the root mass and increased nutrient uptake by the plant. While the use of ectomycorrhizal inocula appears attractive, difficulties with large scale production of these organisms has limited their commercial use.

Given the pressing need in the forestry industry for inoculants capable of enhancing seedling growth and survival on reforestation sites, it is clear that additional strategies for promoting conifer seedling development would be of considerable benefit.

It is an object of the present invention to provide a method for enhancing the growth of conifer seedlings.

It is a another object of the present invention to provide an inoculant composition suitable for promoting the growth of conifer seedlings.

It is a further object of the present invention to provide conifer seed on which has been applied a composition capable of promoting the growth of conifer seedlings.

SUMMARY OF THE INVENTION

In accordance with the present invention it has been found that the growth of conifer seedlings in the greenhouse and in the field can be enhanced when inocula comprising selected bacterial strains are employed. In particular, it has been discovered that a distinct sub-group of bacteria can be isolated from soil in a wide variety of habitats, the members of which sub-group possess the ability to cause increases in growth of conifer seedling roots and shoots. Members of this bacterial sub-group are further distinctively characterized by the ability to inhabit the root zone of conifer seedlings grown in mildly acidic e.g. peat-based, soils and thus are capable of exerting their beneficial effects under those conditions typically experienced in greenhouse and field soils in which conifer seedlings are grown.

To provide for the enhanced growth of conifer seedlings, the growth enhancing bacterial strains may be employed at various stages of conifer seedling production. According to one aspect of the present invention, conifer seed is treated with the bacterial strain prior to planting. According to another aspect of the invention, the bacterial strain is used to treat nursery-grown conifer seedling before transplanting to the reforestation site by applying a suspension of the bacterial strain either to the seedling roots e.g. as a dip, or to the soil in which the seedling is grown e.g. as a soil drench.

DESCRIPTION OF THE PREFERRED EMBODIMENTS

The bacterial strains useful in the present invention are those bacterial strains which cause a statistically significant enhancement of conifer seedling growth, in the context of dry or fresh root weight and shoot weight, seedling height or total plant dry or fresh weight.

Naturally occurring bacterial strains for use in the present invention may be isolated and identified using protocols generally similar to those established for the isolation of root-colonizing bacteria such as the PGPR. Preferably, however, early stages of the generalized isolation procedure are adapted for the more specific purpose of identifying root colonizers beneficial to conifer seedling growth.

Thus, in the first step of the isolation procedure whereby biological samples are collected for screening, the collection of rhizosphere (root-zone) bacteria is favoured by limiting to collection of root-associated soils and root segments per se. Further, to increase the probability of isolating strains adapted for growth in or near the conifer root environment, sample collection may be confined to soil associated with conifer roots and conifer root segments per se. For example, sampling sites such as reforested areas, mature conifer stands or harvested regions thereof and conifer nursery soils are highly desirable areas for sample collection. It should be appreciated, however, that the extraction of samples from areas in which conifers have been grown is not an essential step in the isolation protocol. As shown in the examples herein, bacterial swains isolated from sites other than conifer growth areas and selected originally for their beneficial effects on agronomic crop plants such as canola, soybean, celery, tomato and the like, have surprisingly been found to confer effects beneficial to coffer seedling growth.

Following sample collection, conventional laboratory screening procedures may be implemented to isolate single, purified colonies of bacterial strains contained in the samples. Thus, serial dilutions of individual samples are prepared, the diluted samples are plated and incubated on suitable nutrient medium such as tryptic soy agar and then individual colonies are transferred to fresh media as necessary to provide "biologically pure" bacterial cultures i.e. cultures in which virtually all the bacterial cells present are of the selected strain. Such cultures may be stored, for example at −80C. in glycerol, for subsequent use.

Where samples have been collected exclusively from conifer growth sites, it will be desirable to isolate at least one representative of all distinct colonies obtained from those samples. Where, however, the samples to be laboratory-screened have been collected from other than conifer growth sites, e.g. from soils associated with the roots of agronomic crops or grasses, it is desirable to prescreen those samples before they arc plated by incorporating selection criteria that favour isolation of strains more apt to be beneficial to conifer seedling growth, in order to reduce subsequent screening efforts. To select for those bacterial strains adapted for growth in the conifer rhizosphere, conifer seedlings, preferably of the species for which growth-enhancing bacterial strains arc desired, may be grown directly in the collected soil samples before those samples are plated. The screening process may then continue with only those samples collected from the roots or root-associated soil of the laboratory-grown seedlings. In addition, soils collected from sites other than conifer growth sites are also preferably screened to select for strains tolerant to the cold temperatures and mildly acidic environments characteristic of conifer soils. For example, the nutrient medium in which the samples are initially cultured may be acidified to a pH in the range from about pH 4.5 to about pH 6.5 to select for acid-tolerant strains. Further, the cultured samples may be incubated at temperatures in the range from about 4 C to 14 C to select for cold-tolerant strains.

After applying the laboratory screening protocol to the raw or prescreened soil and root samples, the purified strains are then tested under greenhouse conditions for growth promoting activity in a conifer seedling assay. In a conifer seedling assay suitable for this purpose, a biologically pure culture of a candidate swain is first transferred to a bacteriological growth medium, cultured for 1–2 days, centrifuged, washed and then mixed with water or buffer solution to create a bacterial suspension for seed treatments. Seeds of a selected conifer species are then treated with the suspension such as by overnight soaking and the treated seeds are planted in individual pots containing a peat-based nutrient mixture such as washed peat and vermiculite (2:1). Such a mixture is typical of mixtures used currently in conifer seedling nurseries. The surface of the mixture in which the treated seed is sown is then covered, as is conventional, with a thin layer of washed, coarse sand to promote germination.

Over the course of from three to four months, seedling growth in the greenhouse is monitored and compared with growth rates of untreated seed grown under the same conditions. Strains which cause a statistically significant increase, relative to controls, in one or more parameters including seedling height and root mass are identified as causing enhancement of conifer seedling growth.

To be useful as inocula for conifer seeds and seedling roots, it is important that the selected bacterial strain is one capable of inhabiting the conifer seedling root zone so that the bacterial strain remains in association with the root, at least for a time sufficient for the seedling to benefit from the bacterial association. Particularly preferred bacterial strains are those capable of colonizing the surface of the seedling roots. It is also especially important that bacterial strains to be used for conifer seed inoculation are able to transfer from the seed to roots developing from the seed.

To select for particularly preferred bacterial strains, the root-colonizing ability of those strains that exhibit growth promoting activity in the greenhouse assay is evaluated in a root-colonizing assay. The root-colonizing assay is conducted in a manner similar to that described by Scher et al, 1984, "A Method for Assessing the Root-Colonizing Capacity of Bacteria on Maize", Can. L Microbiol. 30, pp. 151–157. In general, the assay is performed with rifampicin-resistant mutants of the chosen strain that have been selected on rifampicin-containing media. Root segments excised from conifer seedlings that have grown from seed inoculated with the rifampicin resistant form of the selected bacterial strain are then shaken free of loose soft and weighed. Diluted samples of the root segments are plated on media containing rifampicin and bacterial colonies are counted. Strains preferred for use in the present invention are identified as those which colonize mots at a level of at least 100 colony forming units per gram of conifer seedling root (fresh weight).

Bacterial strains that have been selected by the screening protocols and assays just described are particularly well adapted for use as inocula to cause enhanced growth of conifer seedlings, both in the nursery and in the field. Their ability to colonize the relatively harsh environment of conifer roots and their growth enhancing properties may be used to advantage in connection with a wide variety of conifer species. The bacterial strains may be applied, for example, either as seed treatments or as root dips or soil drenches, to any of the many members of the conifer family including pines, spruces, firs, hemlocks, larches, and yews. For example, included among the pine species that can benefit from the use of the bacterial strains are jack pine, white pine, red pine and Scotch pine. Spruce and fir species that can be treated with the bacterial strains include black spruce, white spruce and Douglas fir and balsam fir.

To capitalize on the beneficial effects offered by the selected bacterial strains, seeds of the selected conifer species are treated to apply to the surface of the seed a bacterial population sufficient to enhance the growth of seedlings emergent therefrom. Seeds may be treated using known techniques such as by soaking in water- or buffer-based bacterial suspensions. The suspension is prepared having regard to the desirability of introducing, onto the seed, a bacterial concentration in the range from about $10^3$ to about $10^3$ cells per seed. Accordingly, suspensions comprising from about $10^3$ to about $10^9$ cells/ml of suspension are appropriate for use in seed treatment and for root treatment as well. Such suspensions may be prepared by culturing the selected bacterial strain in culturing broth as required to reach the stationary growth phase and then collecting and washing to remove media if desired. The desired population of cells is then resuspended in buffer. The buffered suspension per se can be used for seed and root treatments. Alternatively, the washed cells may be suspended in other agronomically acceptable formulations. For example, the cells may be used to inoculate the peat in which the seedlings are to be grown or the inoculated peat may be used to as a seed treatment. Polysaccharide solutions may also be used such as alginate or xanthan gum solutions.

Once treated, the conifer seed may be sown and the conifer seedling nurtured using the regimes conventional in the conifer nursery industry. Typically, the treated seeds are planted individually in containers or pots filled with a nutrient mix of peat and vermiculite, and then grown, with fertilizer and watering as necessary, under controlled greenhouse conditions. After a period of time that can be markedly reduced as a result of inoculation with the selected bacterial strains, but generally in about three months, the 3–6 inch seedlings are typically then moved outdoors for a "hardening" period before being outplanted to the reforestation site.

In accordance with a preferred embodiment of the invention, conifer seedlings may be treated with the selected beneficial bacterial strains before being transplanted to the reforestation site. "Bare root" seedlings i.e. seedlings that are freed from the container and soil in which they have grown, may be treated by dipping the roots thereof in a bacterial suspension prepared as described above for the treatment of conifer seed. As an alternative procedure useful for delivering the bacteria to the roots of containerized seedlings, the soil surrounding the roots may be soaked in a bacterial suspension. By these methods, the bacterial population in the seedling root zone is increased before outplanting, so as to enhance seedling survival and establishment in the early stages of growth at reforestation sites.

EXAMPLES

A variety of bacterial strains selected previously for their ability to promote growth of agronomic crop plants such as rapeseed and soybean were screened initially for their ability to promote seedling growth in selected conifer species and, in a subsequent assay, for their ability to colonize the surface of the seedling roots.

In the following tables and text, internal reference codes are used to identify the tested bacterial strains. The identity of these strains is described in more detail below. It should be understood, unless otherwise stated, that each of the referenced strains was originally isolated from Arctic soil samples collected in the manner described by Lifshitz et al in Appl. Env. Microbiol., Feb. 1986, p. 251–255, incorporated herein by reference, and that each strain was originally selected for its growth promoting and root-colonizing activity on rapeseed as determined by the protocol described by Kloepper et al in Plant Disease, Vol. 72, No. 1, 1988, p. 42–45, also incorporated herein by reference.

Strain 44-9 is a member of the Coryneform taxonomic group, possibly Aureobacterium sp. or Curtobacterium sp.

Strains 36-43, 34-13, 61-9A and 31-12 are all members of the *Pseudomonas fluorescens* species.

Strains GR12-2, GI11-32 and G25-44 are both of the *Pseudomonas putida* species. Strain G11-32 is also noted for its ability to promote the nodulation of legume species such as soybean.

Strain 1-102 is a *Serratia proteamaculans* ss. Quinovora strain also capable of promoting nodulation of soybean (see Scher et al, 1988, Phytopathology, 78, 8, p. 1055–1059). Strain 1-102 was deposited with the American Type Culture Collection in Rockville, Md. on Jan. 27, 1986 under accession number 53448.

Thus, these strains, known to colonize the roots of agronomic crops and to promote the growth thereof, were evaluated for their ability to enhance conifer seedling growth using experimental designs described in more detail below.

Example 1—Growth enhancement of black spruce seedlings in the greenhouse

Seeds of black spruce (*P. marianus*) were soaked in buffered suspensions of randomly selected strains of rhizobacteria known to enhance agronomic crop growth. The seeds were pregerminated in the presence of the bacterial suspension for 12 hours at 4° C., then for 8 days at 10° C. and finally at room temperature until the root emerged. The pregerminated, treated seeds were then planted in 12 paper pots (20 seeds/pot) containing a disease-free mixture of washed sphagnum peat moss and medium vermiculite (7:3) and. placed in the greenhouse. After about 9 weeks, they were transplanted to cups and were fertilized with a 20—20—20 fertilizer blend. Seedling growth was monitored over a 23 week growth period and rated using the parameters indicated in Table 1 below, in which increases in seedling height, seedling stem length and total dry weight of seedlings are reported as % increase relative to control seedlings grown from non-inoculated seed under the same conditions.

TABLE 1

| | | height | | stem length | | dry wt | |
|---|---|---|---|---|---|---|---|
| stain | cfu/seed | 11 wks | 13 wks | 14 wks | 19 wks | 22 wks | 23 wks |
| 44-9 | 5.5 | 4 | 1 | 14 | 11 | 15 | 34 |
| 36-43 | 5.8 | 21 | 22 | 39 | 19 | 18 | 27 |
| GR12-2 | 6.4 | -2 | 2 | -3 | -3 | -4 | -6 |

Under the specified experimental conditions, *Pseudomonas fluorescens* strain 36-43 and the Coryneform bacterium 44-9 demonstrated the ability to promote growth of black spruce seedlings to an extent that is statistically significant. Although noted for its ability to promote growth of agronomic crop plants, *Pseudomonas putida* strain GR12-2 failed to cause increased growth of black spruce seedlings.

Strains 44-9 and 36-43 and other strains noted for their growth promoting effects on agronomic crops were evaluated in subsequent experiments for their ability to enhance the mass of black spruce seedling roots. In these experiments, black spruce seeds were coated with a bacteria/ alginate preparation (0.05 mL preparation/g of seed), sown in containers of washed peat and medium vermiculite (2:1) and then covered with coarse, washed sand. The results, scored 40 weeks after planting, are reported in Table 2 as percent increase in root dry weight as compared with non-treated control seed grown under the same experimental conditions.

TABLE 2

| strain | cfu/seed | root dwt |
| --- | --- | --- |
| 44-9 | 5.08 | 22 |
| 36-43 | 3.62 | 11 |
| GR12-2 | 3.86 | 4 |
| 34-13 | 3.74 | 5 |
| 61-9A | 4.21 | 25 |
| 1-102 | 4.45 | 13 |
| 31-12 | 3.25 | −9 |
| Control | 0 | 0 |

It will be noted that strains GR12-2, 34-13 and 31-12 failed to cause a statistically significant increase in root dry weight under these experimental conditions. It will be appreciated that strains noted for their ability to promote the growth of agronomic crop plants are not necessarily useful also as conifer seedling growth enhancers. The conifer seedling growth assay is accordingly an important and useful means for selecting bacterial strains useful in the present invention. It will be further noted that strain 61-9A, a Pseudornonas species and strain 1-102, a *Serratia proteamaculans* ss. Qinovora strain, also exhibit beneficial effects on root growth of black spruce seedlings.

Seedling growth enhancement caused by strain 36-43 and by strain 44-9 was confirmed in subsequent experiments performed in substantially the same manner just outlined but employing a fertilization regime and seedling containers used conventionally in conifer seedling nurseries.

Example 2—Growth Enhancement of Black Spruce Seedlings in the Field

To evaluate the effects of bacterial strains on seedling growth in the field, roots of black spruce seedlings and white spruce seedlings gown in the nursery were treated either by soaking the bare roots for 30–45 minutes in a water-based suspension of a bacterial strain selected from 44-9 and 36-43, or by pipeting the bacterial suspension directly into the potted soil in which the seedlings were grown. Treated seedlings were then planted outdoors, in clay/loam soil, as treated i.e. either in the pot or bare-root. One lot of untreated seedlings was planted similarly and another lot of untreated seedlings was measured for initial fresh and dry weights. Biweekly measurements of total height of each planted seedling were taken and sample seedlings were harvested at 8 week and 16 week intervals for analysis.

Analysis of the treated black spruce and white spruce seedlings after 16 weeks of field growth indicated that root fresh weight in particular, was increased to a statistically significant extent relative to untreated controls. Increases were also noted for shoot fresh weight and total plant fresh weight. Treatment by root soaking was evidently superior to treatment by soil soaking as an inoculation technique, although soil soaking did provide statistically significant increases in black spruce seedling height.

Example 3—Growth Enhancement of Jack Pine Seedlings in the Greenhouse

Using the same protocols and bacterial strains described in example 1, the effects of those strains on jack pine seedling growth were evaluated. Results are reported in Table 3 as % increase in seedling height and root and shoot dry weight relative to seedlings grown from untreated seed under the same conditions.

TABLE 3

| strain | cfu/seed | height | | | dry weight | |
| --- | --- | --- | --- | --- | --- | --- |
| | | 6 wks | 9.5 wks | 11.5 wks | shoot | root |
| 44-9 | 4.41 | 16 | 11 | 7 | 15 | 5 |
| 36-43 | 5.80 | 6 | 1 | 8 | −2 | 14 |
| GR12-2 | 3.79 | 5 | 11 | 10 | 35 | 43 |

It will be noted that whereas GR12-2 was unable to cause significant increases in black spruce seedling growth, treatment of jack pine seed with this strain caused a significant increase in the root dry weight of jack pine seedlings. It will be further noted that strains 44-9 and 36-43 are both able to enhance jack pine seedling growth.

To evaluate whether strain 44-9 was able to colonize roots of jack pine seedlings, seeds were treated with a water-based suspension of a rifampicin resistant mutant of 44-9. As a result of treatment, seeds had been coated with $\log_{10} 5.8$ cells. Seedlings were then grown according to the procedures outlined in Example 1 and harvested at intervals of 2, 4 and 7 weeks. Roots from which loose soil had been removed were weighed and then placed in buffer, samples thereof were diluted 100-fold, and the diluted samples were then plated on rifampicin-containing media and grown for three days at room temperature. Colonies were then counted.

Results of the assay revealed that, even seven weeks after planting, strain 44-9 was present on jack pine seedling roots to the extent of about $\log_{10} 4$ cells per gram of root (fresh weight).

Example 4—Further characterization of Bacterial Strains that promote conifer seedling development.

Strain GR12-2 is an arctic diazotrophic, nitrogen-fixing member of the species *Pseudomonas putida*, which was isolated from the rhizosphere of an eastern Canadian habitat. Colony morphology is characterized as smooth, entire, with fluorescent green pigment on Pseudomonas agar F. Cells are rod-shaped and typically exhibit one pointed end. Gram stain reaction is negative. A representative specimen of GR12-2 was deposited with the American Type Culture Collection in Rockville, Md., USA on Nov. 18, 1986 under accession number 53555. Samples thereof are available to those entitled thereto in accordance with the terms of the Budapest Treaty.

Strain 36-43 is also an arctic diazotrophic, nitrogen-fixing pseudomonad but belonging to the species *Pseudomonas fluorescens*. Colony morphology is characterized as fluorescent, yellowish beige, mucoid, circular, regular margin, shiny and flat, with 2–6 mm diameter. Cells are medium-sized and rod-shaped, highly motile, not too long but slender and predominantly single. Gram stain reaction is negative. A representative specimen of strain 36-43 was deposited with the American Type Culture Collection on Apr. 25, 1990, under accession number 55034. Samples thereof are available to those entitled thereto under the terms of the Budapest Treaty.

Strain 44-9 exhibits colony morphology characterized as non-fluorescent, bright yellow, creamy, circular, regular margin, convex, shiny, with 2–3 mm diameter. Cells are pleomorphic, club-shaped, small rods in old cultures with some large cocci visible. Young cells are negative in the Gram stain but stain variably with age. Precise identification is difficult, but strain 44-9 appears to have many of the taxonomic attributes of Arthrobacter or Aureobacterium members of the Coryneform group. A representative specimen of strain 44-9 was deposited with the American Type Culture Collection on Apr. 25, 1990 under accession number 55035. Samples thereof are available to those entitled thereto under the terms of the Budapest Treaty.

Other taxonomically relevant characteristics of strains 44-9, 36-43 and GR12-2 are revealed in the Table below:

| Character | Reaction* | | |
|---|---|---|---|
| | GR 12-2 | 36-43 | 44-9 |
| Growth in pH 6 | + | + | + |
| Growth in pH 8 | + | + | − |
| Growth at 4° C. | + | + | + |
| Growth at 30° C. | + | + | + |
| Growth at 37° C. | − | + | + |
| Growth in 3% NaCl | − | | |
| Doubling time at 25° C. | 90 minutes | | |
| Nitrogenase at 4° C. | + | | |
| Nitrogenase at 25° C. | + | | |
| Nitrogenase at 30° C. | − | | |
| Growth in MacConkey agar | + | + | − |
| Growth in skim milk | + | | |
| growth on acetate as SCS | + | | |
| Phenylalanine deamination | − | | |
| Nitrate to nitrite | − | − | |
| Nitrite reduction | − | | |
| Nitrite to $N_2$ | − | | |
| Arginine (Mollers) | + | + | |
| Gelatinase | − | + | − |
| Urease | − | − | − |
| Cytochrome oxidase | + | | |
| Lysine decarboxylase | − | | |
| Ornithine decarboxylase | − | | |
| Lecithinase | − | | |
| Phosphatase | + | | − Pase |
| Catalase | + | + | + Catalase |
| Oxidase | + | + | − |
| Melobiose | + | | |
| β-glucosidase | − | | |
| Deoxyribonuclease | − | − | − |
| Tryptophase deaminase | − | − | |
| Mannitol acidification | + | − | − |
| Sorbitol acidification | − | | |
| Inositol acidification | − | | |
| D-mannose | + | | + |
| L-rhamnose | − | − | |
| D-ribose | + | | − (Simmons) |
| Growth on Simmons citrate | + | | |
| Growth on dl-hydroxybutyrate | + | | |
| Growth on 0.05% centrimide | + | | |
| Growth on Antibiotic: | | | |
| Kanamycin (10 ppm) | − | − | − |
| Chloramphenicol (10 ppm) | − | − | − |
| Tetracycline (10 ppm) | − | − | − |
| Fluorescein production | + | + | − |
| Other pigments | − | − | Yellow |
| $H_2S$ production | − | − | + |
| Indole production | − | − | − |
| Pyocyanin production | − | | |
| Pyoverdin production | + | | |
| 3-ketolactose from lactose | − | | |
| Casein hydrolysis | − | | |
| Starch hydrolysis | − | − | |
| Tween 20 hydrolysis | + | + | |
| Tween 80 hydrolysis | + | − | |
| Testosterane degradation | − | | |

| Character | Reaction* | | |
|---|---|---|---|
| | GR 12-2 | 36-43 | 44-9 |
| Tyrosine degradation | + | | |
| Fermentation with D-glucose | − | | |
| Formation of acid from**: | | | |
| L-arabinose | + | − | + |
| Cellobiose | K | | + |
| Ethanol | + | | |
| D-fructose | + | | |
| D-glucose $AO_2$ | + | − | + |
| D-glucose $AnO_2$ | − | | − |
| Glycerol | + | | + |
| I-inositol | K | | |
| D-mannitol | + | − | − |
| D-mannose | + | | + |
| L-rhamnose | + | | − |
| D-ribose | + | | |
| Lactose | K | | − |
| Maltose | K | | + |
| Sucrose | K | − | + |
| Trehalose | K | | + |
| D-xylose | + | | + |
| Control | K | | |

*Reactions: +, growth and (or) activity; −, no growth and (or) no activity;
**K = alkaline; + = acid; − = no change Those skilled in the art will appreciate that variants of the deposited strains i.e. those shins particularly preferred for use in the present invention, may arise through spontaneous or artificially induced mutation. Variants may also be produced using the DNA mediated transformation techniques now used commonly in the bacterial art to introduce genes coding for desirable expression products. Provided that the variants of the deposited sums retain the ability to enhance conifer seedling growth, such variants may be employed in accordance with the present invention.

We claim:

1. A method for growing a conifer seedling, which comprises the steps of:
   selecting a conifer seed; and
   treating said conifer seed, prior to planting thereof, with a bacterial strain of Coryneform, Pseudomonas or Serratia that enhances the root growth of a seedling of said conifer seed.

2. The method according to claim 1 wherein the conifer seed is treated by soaking in a suspension comprising said bacterial strain.

3. The method according to claim 1 wherein the treated coffer seed is a pine seed.

4. The method according to claim 1 wherein the treated conifer seed is a spruce seed.

5. A method for enhancing the root growth of a transplanted conifer seedling, which comprises the steps of:
   selecting a conifer seedling; and
   treating the roots of said conifer seedling with a bacterial strain of Coryneform, Pseudomonas or Serratia that enhances the root growth of said conifer seedling.

6. The method according to claim 5 wherein the conifer seedling roots are treated by soaking in a suspension of said bacterial strain.

7. The method according to claim 5 wherein the conifer seedling roots are treated by delivering a suspension of said bacterial strain to soil in which the conifer seedlings are grown.

8. A modified conifer seed, said conifer seed having been modified by treatment with an isolated, biologically pure culture of a strain of Coryneform, Pseudomonas or Serratia which enhances the root growth of a seedling of said conifer seed.

9. A modified conifer seed according to claim 8 which is a pine seed.

10. A modified conifer seed according to claim 8 which is a spruce seed.

11. A modified conifer seed according to claim 8 wherein said seed is treated with an isolated, biologically pure culture of bacterial strain 44-9 or a growth-enhancing spontaneous mutant thereof.

12. A modified conifer seed according to claim 8 wherein said seed is treated with an isolated, biologically pure culture of bacterial strain 36-43 or a growth-enhancing spontaneous mutant thereof.

13. A modified conifer seed as defined in claim 8 wherein said seed is a black spruce seed treated with an isolated, biologically pure culture of a bacterial strain selected from the group consisting of strain 44-9 and strain 36-43.

14. A modified conifer seed as defined in claim 8 wherein said seed is a jack pine seed treated with an isolated, biologically pure culture of a bacterial strain selected from the group consisting of strain 44-9 and strain 36-43.

15. A method of enhancing conifer seedling root growth, comprising the steps of:

selecting a conifer seeding; and treating the roots of said conifer seedling with a bacterial culture of Coryneform, Pseudomonas or Serratia that enhances the root growth of said conifer seedling.

16. A method of enhancing conifer seedling root growth as claimed in claim 15, wherein said bacterial culture is a biologically pure culture of bacterial strain 44-9 or a biologically pure culture of bacterial strain 36-43.

* * * * *